United States Patent [19]

Yamaguchi

[11] 4,212,826

[45] Jul. 15, 1980

[54] PROCESS FOR PRODUCING CYSTEAMINES AND/OR CYSTAMINES

[75] Inventor: Hachiro Yamaguchi, Hiroshima, Japan

[73] Assignee: Wakunaga Yakuhin Kabushiki Kaisha, Osaka, Japan

[21] Appl. No.: 45,679

[22] Filed: Jun. 5, 1979

[30] Foreign Application Priority Data

Jun. 16, 1978 [JP] Japan ................................. 53-72060

[51] Int. Cl.$^2$ .............................................. C07C 85/24
[52] U.S. Cl. .............................................. 260/583 EE
[58] Field of Search ............. 260/583 EE, 608, 609 R

[56] References Cited

U.S. PATENT DOCUMENTS 2,689,867   9/1954   Mahan ........................... 260/583 EE

FOREIGN PATENT DOCUMENTS 53-3365   6/1978   Japan ................................. 260/583 EE

OTHER PUBLICATIONS

Houben-Weyl, "Methoden Der Organischen Chemie", Band IX, pp. 8-11 (1955).
Horoshima University, Engineering Department Research Report, vol. 26, No. 2, pp. 1-5.
Journal of the Chemical Society of Japan, Chemistry and Industrial Chemistry, 1979, (1), pp. 149-151 (1979).
Journal of the Chemical Society of Japan, Chemistry and Industrial Chemistry, 1979, (4), pp. 517-521 (1979).

*Primary Examiner*—John Doll
*Attorney, Agent, or Firm*—Wenderoth, Lind & Ponack

[57] ABSTRACT

Specific cysteamines and/or cystamines are produced by a process which comprises causing (A) an aminoalkyl sulfate ester and (B) hydrogen sulfide and an alkali polysulfide formed from an alkali hydrogen sulfide and sulfur to react.

5 Claims, No Drawings

PROCESS FOR PRODUCING CYSTEAMINES AND/OR CYSTAMINES

BACKGROUND OF THE INVENTION

1. Field of the Art

This invention relates to the production of cysteamines and/or cystamines.

Cystamines are readily formed by oxidation of their corresponding cysteamines as in the example indicated in the following formula (1). Conversely, cysteamines are readily formed by reduction of their corresponding cystamines.

$$2H_2N-CH_2CH_2-SH \underset{\text{reduction}}{\overset{\text{oxidation}}{\rightleftarrows}} \begin{array}{c} H_2N-CH_2CH_2-S \\ | \\ H_2N-CH_2CH_2-S \end{array} \quad (1)$$

cysteamine → cystamine

Since the oxidation or reduction as indicated in Formula (1) readily progresses even in vivo, these cysteamine and cystamine compounds are attracting much attention as medicinal substances exhibiting various physiological activities. For example, a cysteamine and certain related compounds are useful as substances having protective action relative to harmful effects of radiation.

Accordingly, there have been numerous proposals relating to the production of these compounds.

2. Prior Art

I have previously proposed a process (as disclosed in Japanese Patent Publication No. 3365/1978) for producing cysteamines by heating and reacting an aminoalkyl sulfate ester and a compound having hydrogen sulfide ions ($\ominus SH$). This prior invention succeeded in producing cysteamines with greater facility and higher yield than processes previously known at that time by heating an aminoalkyl sulfate ester and a hydrogen sulfide such as ammonium hydrogen sulfide or potassium hydrogen sulfide in a solvent such as water or water-containing alcohol.

It was discovered, however, that a problem is sometimes encountered in the practice of this prior invention in that, when an alkali hydrogen sulfide such as potassium hydrogen sulfide or sodium hydrogen sulfide is used as a source of the hydrogen sulfide ions, thioethers are easily formed as accompanying by-products in addition to the cysteamines and/or cystamines depending on the reaction conditions.

SUMMARY OF THE INVENTION

It is an object of this invention to solve the above mentioned problem accompanying the above described prior invention. This object can be achieved by using, instead of an alkali hydrogen sulfide by itself, an alkali polysulfide formed together with hydrogen sulfide from the alkali hydrogen sulfide to which sulfur has been added.

According to this invention, briefly summarized, there is provided a process for producing cysteamines of the formula $$R^1_{\phantom{1}}\diagdown_{\phantom{1}}\phantom{N}R^3 \atop R^2_{\phantom{2}}\diagup^{\phantom{2}}N\!\!\!-\!\!(C)_n\!\!-\!\!SH \atop \phantom{R^2}\phantom{\diagup}\phantom{N}R^4 \qquad (I)$$

and/or cystamines of the formula $$\left[ R^1_{\phantom{1}}\diagdown_{\phantom{1}}\phantom{N}R^3 \atop R^2_{\phantom{2}}\diagup^{\phantom{2}}N\!\!\!-\!\!(C)_n\!\!-\!\!S \atop \phantom{R^2}\phantom{\diagup}\phantom{N}R^4 \right]_2, \qquad (II)$$

wherein n is 1, 2, or 3, and $R^1$, $R^2$, $R^3$, and $R^4$ are respectively and independently H or $CH_3$, a plurality of $R^3$ and $R^4$ not necessarily being the same when n is 2 or 3, said process being characterized in that (A) an aminoalkyl sulfate ester and (B) hydrogen sulfide and an alkali polysulfide formed from an alkali hydrogen sulfide and sulfur are caused to react.

I have found that, by using, instead of the alkali hydrogen sulfide in the process of the aforementioned prior invention, an alkali polysulfide formed together with hydrogen sulfide from the alkali hydrogen sulfide and sulfur, the formation of thioethers as a by-product can be suppressed, and cysteamines and/or cystamines of high purity are obtained.

The starting materials aminoalkyl sulfate esters, alkali hydrogen sulfide and sulfur are all inexpensive, and, moreover, the reaction proceeds gently and easily, whereby, together with the above mentioned advantageous feature of high purity, this invention affords advantageous production of useful cysteamines and/or cystamines.

The nature, utility, and further features of this invention will be more clearly apparent from the following detailed description beginning with a consideration of general aspects of the invention and concluding with specific examples of practice illustrating preferred embodiments thereof.

DETAILED DESCRIPTION OF THE INVENTION

1. Reaction process

One example of synthesis of a cysteamine from aminoethyl sulfate ester, hydrogen sulfide, and sodium polysulfide (m=2 to 8) according to the process of this invention is indicated by the following Formula (2).

$$\begin{array}{c} CH_2\!-\!CH_2 \\ O\diagup\phantom{xx}\diagdown\overset{\oplus}{NH_3} \\ \diagdown\phantom{xxx}\diagup \\ SO_2\!-\!O^{\ominus} \end{array} + Na\!-\!(S)_m\!-\!Na + H_2S \xrightarrow[\text{in aqueous solution}]{\text{heating}}$$

$$\begin{array}{c} CH_2\!-\!CH_2 \\ HS\diagup\phantom{xx}\diagdown NH_2 \end{array} + NaO\!-\!SO_2\!-\!ONa \qquad (2)$$

2. Starting materials

2-1. Aminoalkyl sulfate ester

The aminoalkyl sulfate ester used as the principal starting material can be represented by the following Formula III, as is apparent from the general formulas I and II set forth hereinbefore.

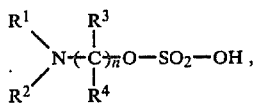

where, $R^1$ through $R^4$ and n are defined as in the case of the Formulas (I) and (II).

As is apparent from the above given reaction Formula (2), the aminoalkyl sulfate ester participating in the reaction of this invention is a mono ester or acid ester, and may thus probably be in a form of an intra-molecular salt. As long as there is no adverse effect on the reaction of the hydrogen sulfide and the alkali polysulfide according to this invention, however, the aminoalkyl sulfate ester can be in the form of a diester or diaminoalkyl sulfate ester, of a salt with a suitable basic substance such as an amine salt, an ammonium salt, an alkali metal salt, or some other form instead of the fundamental monosulfate or acid sulfate of the above Formula III. However, it can be said that the form of Formula III is preferable in view that contamination of the reaction system is made minimum.

Specific examples of aminoalkyl sulfate esters of this character are shown with respect to an aminoalkyl group as follows: 2-aminoethyl ($R^1$ through $R^4$=H, n=2), 3-aminopropyl ($R^1$ through $R^4$=H, n=3), 2-aminopropyl ($R^1$ and $R^2$=H, $R^3$=H, $R^4$=CH$_3$, $R^{3'}$ and $R^{4'}$=H, n=2, $R^{3'}$ and $R^{4'}$ indicating $R^3$ and $R^4$ of a second pair where n is 2), 2-amino-2-methylpropyl ($R^1$ and $R^2$=H, $R^3$ and $R^4$=CH$_3$, $R^{3'}$ and $R^{4'}$=1, n=2), 2-methylaminoethyl ($R^1$=H, $R^2$=CH$_3$, $R^3$ and $R^4$=H, n=2), and 2-dimethylaminoethyl ($R^1$ and $R^2$=CH$_3$, $R^3$ and $R^4$=H, n=2). Further particulars are set forth in Hiroshima University, Engineering Department Research Report, Vol. 26, No. 2, PP 1 to 5.

An aminoalkyl sulfate ester of this character is a compound which can be readily prepared by a known process from an acid sulfate salt of the corresponding aminoalkyl alcohol. More specifically, by heating to a temperature of the order of 100° C. an aqueous solution of, for example, an aminoalkyl alcohol acid sulfate salt formed from an aminoalkyl alcohol and sulfuric acid, an aminoalkyl sulfate ester can be obtained as an aqueous solution or as a suspension thereof. In this invention, for the aminoalkyl sulfate ester, pure crystals of the same can, of course, be used, but the heated reaction liquor of aqueous solution of the aminoalkyl alcohol acid sulfate salt, also, can be used as it is.

2-2. Alkali polysulfide and hydrogen sulfide

The alkali polysulfide and the hydrogen sulfide can be readily obtained in the form of an aqueous solution thereof by saturating an aqueous solution of an alkali with hydrogen sulfide gas (which is the step of forming the alkali hydrogen sulfide) and adding sulfur to this solution.

The "alkali" of the alkali polysulfide used in this invention means, principally, an alkali metal, but one part or the whole thereof may be substituted by ammonium or some other alkali-equivalent substance provided that there is no departure from or impairment of the spirit and purport of this invention. The degree of sulfidation m (reference being made to reaction Formula (2)) is of the order of 2 to 8.

3. Reaction

The above described two starting materials are preferably reacted in an aqueous medium. The term "aqueous medium" as used herein means, in addition to case where it comprises substantially only water, mixtures of water and a water-miscible organic solvent such as, for example, an alcohol, an ether, a ketone, dimethylformamide, dimethylacetoamide, and the like. The mole ratio of the alkali polysulfide used to the aminoalkyl sulfate ester is of the order of 1 to 3.

The reaction temperature is desirably of the order of 60° to 80° C. The required reaction time at a reaction temperature of approximately 70° C. is from 40 to 50 minutes. The yield is of the order of 80 to 90 percent.

Since a cystamine is formed by the oxidation of a cysteamine, as indicated hereinbefore (reaction Formula (1)), cysteamines and cystamines can be produced as desired by controlling the reaction atmosphere. More specifically, a cysteamine compound having a SH group is readily oxidized in air and is transformed into a cystamine compound having a —S—S— group. For this reason, in order to obtain a cysteamine compound, it is necessary to carry out reaction and treatment in a stream of a non-oxidative gas or an inert gas such as nitrogen gas, but in the case where a cystamine compound is to be obtained, a stream of an inert gas is not necessary. In this connection, it is necessary to thoroughly oxidize the SH group with the use of a hydrogen peroxide solution or the like thereby to effect the change to the —S—S— group.

4. Formed products

While, in the examples set forth hereinafter, each of the formed compounds is obtained as a hydrochloride, this can be readily changed by a known process into a compound of the form of a free amine. Furthermore, it can be readily changed also into an inorganic acid salt other than a hydrochloride or an organic acid salt.

Cysteamine hydrochlorides and cystamine hydrochlorides thus synthesized are shown respectively in Tables 1 and 2.

Table 1

| Chemical name | Chemical formula | Melting Point (°C.) |
|---|---|---|
| 2-amino-ethanethiol hydrochloride (cysteamine) | HS—CH$_2$—CH$_2$—NH$_2$ . HCl | 60–70 |
| 3-amino-1-propanethiol hydrochloride | HS—CH$_2$—CH$_2$—CH$_2$—NH$_2$ . HCl | 68.0–68.5 |
| 2-amino-1-propanethiol hydrochloride | HS—CH$_2$—CH(NH$_2$ . HCl)—CH$_3$ | 92.0 |
| 2-amino-2-methyl-1-propanethiol hydrochloride | HS—CH$_2$—C(CH$_3$)(CH$_3$)(NH$_2$ . HCl) | 180–182 |

Table 1-continued

| Chemical name | Chemical formula | Melting Point (°C.) |
|---|---|---|
| 2-methylamino-ethanethiol hydrochloride | HS—CH$_2$—CH$_2$—NHCH$_3$ . HCl | (hygroscopic) |

Table 2

| Chemical name | Chemical formula | Melting Point (°C.) |
|---|---|---|
| bis(2-aminoethyl)disulfide hydrochloride (cystamine) | S—CH$_2$CH$_2$—NH$_2$<br>\|              . 2HCl<br>S—CH$_2$CH$_2$—NH$_2$ | 200–203 |
| bis(3-aminopropyl)disulfide hydrochloride | S—CH$_2$CH$_2$CH$_2$—NH$_2$<br>\|                   . 2HCl<br>S—CH$_2$CH$_2$CH$_2$—NH$_2$ | 218–219 |
| bis(2-amino-2-methylethyl)disulfide hydrochloride |         CH$_3$<br>        \|<br>S—CH$_2$CH—NH$_2$<br>\|             . 2HCl<br>S—CH$_2$CH—NH$_2$<br>        \|<br>        CH$_3$ | 213–214 |
| bis(2-amino-2,2-dimethylethyl)-disulfide hydrochloride | CH$_3$    CH$_3$<br>   \ /<br>S—CH$_2$—C—NH$_2$<br>\|             . 2HCl<br>S—CH$_2$—C—NH$_2$<br>   / \<br>CH$_3$    CH$_3$ | |
| bis(2-methylaminoethyl)disulfide hydrochloride | S—CH$_2$CH$_2$—NHCH$_3$<br>\|                . 2HCl<br>S—CH$_2$CH$_2$—NHCH$_3$ | 204–205 |

In order to indicate more fully the nature and utility of this invention, the following examples of specific practice constituting preferred embodiments of the invention are set forth, it being understood that these examples are presented as illustrative only and that they are not intended to limit the scope of the invention.

EXAMPLE 1

To 61 grams (g.) of 2-amino-ethanol, 50 g. of water is added to form an aqueous solution. As this solution is stirred in a cooled state, a 50-percent aqueous sulfuric acid is added thereto in a quantity which is twice that required for neutralization, methyl red being used as an indicator. The resulting solution is concentrated under reduced pressure over a hot-water bath until crystals of the sulfate ester begin to appear. This 2-amino-ethanol sulfate ester suspension is designated a first liquor.

Separately, 100 g. of sodium hydroxide is dissolved in 200 g. of water to form a solution, into which hydrogen sulfide gas is introduced to saturation. Thereafter, to the solution thus obtained, a solution formed by dissolving 32 g. of sulfur powder in 150 ml. of ethanol is added. The resulting sodium polysulfide solution is designated a second liquor.

The second liquor is added to the first liquor, and the resulting liquor is subjected to refluxing at 70° C. for 40 hours. The resulting reaction liquor is neutralized with 2 N hydrochloric acid, and the sulfur thus precipitated is separated by filtration. A 10-percent barium chloride solution is added to the sulfur thus separated thereby to remove the sulfate ions as barium sulfate. The filtrate is concentrated under reduced pressure and, after a small quantity of methanol is added thereto, is filtered. To the solution thus obtained, 3 percent aqueous hydrogen peroxide is added thereto, and the resulting solution is dried under reduced pressure. Recrystallization of the resulting dried product is carried out from isopropanol, whereupon 90.1 g. of a cystamine hydrochloride of a melting point of 203° to 206° C. is obtained. The yield is 80 percent.

EXAMPLE 2

141 g. of cyrstals of 2-aminoethanol sulfate are dissolved in a solution of 100 g. of sodium hydroxide in 400 g. of water, and, into the solution thus obtained and being cooled with ice, hydrogen sulfide gas is blown to saturation. Then, to this solution, a liquor obtained by adding 32 g. of sulfur powder to 150 ml. of ethanol is added. The resulting liquor is maintained at 70° C. for 40 hours and thus caused to react. The liquor is thereafter neutralized with 2 N hydrochloric acid and then filtered. The resulting filtrate is concentrated under reduced pressure and dried. As a result, 102 g. of a mixture of a cysteamine hydrochloride and a cystamine hydrochloride is obtained. The yield is 90 percent.

EXAMPLE 3

As 195 g. of a 50-percent aqueous solution of 2-amino-2-methyl-propanol is stirred in a cooled state, a 50-percent solution of sulfuric acid is added thereto in a quantity which is twice that required for neutralization, methyl red being used as an indicator. The resulting solution is concentrated under reduced pressure over a hot-water bath. The liquor thus obtained is designated a first liquor.

Separately, into a solution of 140 g. of potassium hydroxide in 200 g. of water, hydrogen sulfide gas is blown to saturation. Thereafter, a solution of 32 g. of sulfur dissolved in 150 ml. of ethanol is added to the resulting solution. The liquor thus obtained is designated a second liquor.

The second liquor is added to the first liquor, and the resulting liquor is maintained at a temperature of 65° to 70° C. for 45 hours, after which it is concentrated under reduced pressure. After this concentrated liquor is neutralized with 2 N hydrochloric acid, it is filtered to remove solids, and the filtrate is further concentrated to dryness in a stream of nitrogen gas under reduced pressure. The solid thus obtained is recrystallized from isopropanol, whereupon 130 g. of crystals of 2-amino-2-methyl-1-propanethiol hydrochloride of a melting point of 180° to 182° C. are obtained. The yield is 91 percent.

EXAMPLE 4

163 g. of crystals of 2-amino-1-propanol acid sulfate are added into 500 g. of a 20-percent aqueous solution of sodium hydroxide. Then hydrogen sulfide gas is blown into the resulting liquor to saturation while cooling with ice is carried out. To the resulting liquor is added a liquor formed by adding 32 g. of sulfur powder to 150 ml. of ethanol, and the liquor thus obtained is caused to react by maintaining it in a stream of nitrogen at 70° C. for 40 hours. After the resulting liquor is neutralized with 2 N hydrochloric acid, it was filtered, and the filtrate is concentrated to dryness in a stream of nitrogen gas under reduced pressure. The solid thus obtained is recrystallized from isopropanol, whereupon 114 g. of crystals of 2-aminopropane-1-thiol hydrochloride of a melting point of 92.0° C. are obtained. The yield is 90 percent.

What I claim is:

1. A process for producing cysteamines of the formula

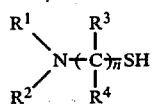 (I)

and/or cystamines of the formula

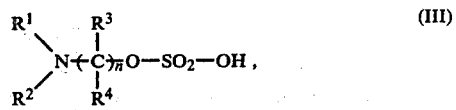 (II)

wherein n is 1, 2, or 3, and $R^1$, $R^2$, $R^3$, and $R^4$ are respectively and independently H or $CH_3$, a plurality of $R^3$ and $R^4$ not necessarily being the same when n is 2 or 3, which process comprises reacting (A) an aminoalkyl sulfate ester and (B) hydrogen sulfide and an alkali polysulfide formed from an alkali hydrogen sulfide and sulfur.

2. A process as set forth in claim 1 in which the aminoalkyl sulfate ester (A) is represented by the formula

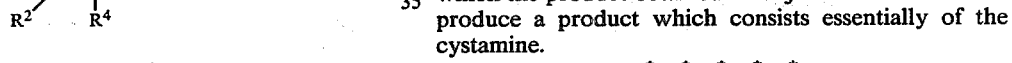 (III)

where, $R^1$, $R^2$, $R^3$, and $R^4$ and n are respectively as defined with respect to Formulas (I) and (II).

3. A process as set forth in claim 1 in which the reaction is carried out in an aqueous medium and at a molar ratio of the alkali polysulfide to the aminoalkyl sulfate ester of 1 to 3.

4. A process as set forth in any of the claims 1 to 3 in which the reaction is conducted under a non-oxidative atmosphere to obtain the product which consists essentially of the cysteamine.

5. A process as set forth in any of claims 1 to 3 in which the product obtained is subjected to oxidation to produce a product which consists essentially of the cystamine.

* * * * *